United States Patent [19]
Forbes et al.

[11] Patent Number: 5,922,733
[45] Date of Patent: Jul. 13, 1999

[54] PYRIDIL CARBOXAMIDES AS 5HT2B/2C RECEPTOR ANTAGONISTS

[75] Inventors: Ian Thomson Forbes, Stevenage; Graham Elgin Jones, Hertford; Francis David King, Bishops Stortford; Peter Ham, Harlow; David Thomas Davies, Ware, all of United Kingdom; Angela Moghe, Melville Park, Singapore

[73] Assignee: SmithKline Beecham p.l.c., Brentford, United Kingdom

[21] Appl. No.: 08/765,933

[22] PCT Filed: Jul. 6, 1995

[86] PCT No.: PCT/EP95/02637
§ 371 Date: Jun. 30, 1997
§ 102(e) Date: Jun. 30, 1997

[87] PCT Pub. No.: WO96/02537
PCT Pub. Date: Feb. 1, 1996

[30] Foreign Application Priority Data

Jul. 13, 1994 [GB] United Kingdom ........... 9414139

[51] Int. Cl.$^6$ .................... A01N 43/42; C07D 401/00
[52] U.S. Cl. .................... 514/310; 514/313; 514/314; 546/196; 546/197; 546/198; 546/199
[58] Field of Search ................. 546/196, 197, 546/198, 199; 514/310, 313, 314

[56] References Cited

U.S. PATENT DOCUMENTS

| | | | |
|---|---|---|---|
| 4,686,224 | 8/1987 | Melvin, Jr. | 514/275 |
| 4,730,004 | 3/1988 | Kadin | 514/418 |

FOREIGN PATENT DOCUMENTS

| | | |
|---|---|---|
| 0 610 553 A1 | 8/1994 | European Pat. Off. . |
| WO 92/05170 | 4/1992 | WIPO . |
| WO 94/14801 | 7/1994 | WIPO . |
| WO 05/01976 | 1/1995 | WIPO . |

OTHER PUBLICATIONS

Forbes, et al., "5–Methyl–1–(3–pyridylcarbamoyl)–1,2,3,5–tetrahydropyrrolo[2,3–f]indole: A Novel 5–HT$_{2C}$/5–HT$_{2B}$ Receptor Antagonist with Improved Affinity, Selectivity, and Oral Activity", (1995), J. Med. Chem. 38(14), pp. 2524–2530.

Palmer, et al., "Tyrosine Kinase Inhibitors. 4. Structure–Activity Relationships among N–and 3–Substituted 2,2'–Dithiobis(1H–indoles) for in vitro Inhibition of Receptor and Nonreceptor Protein Tyrosine Kinases", (1995), J. Med. Chem. 38(1), pp. 58–67.

*Primary Examiner*—Mukund J. Shah
*Assistant Examiner*—Tamthom N. Truong
*Attorney, Agent, or Firm*—Linda E. Hall; Stephen A. Venetianer; Charles M. Kinzig

[57] ABSTRACT

Novel heterocyclic compounds having pharmacological activity, processes for their preparation, to compositions containing them and to their use in the treatment of CNS disorders are disclosed.

8 Claims, No Drawings

PYRIDIL CARBOXAMIDES AS 5HT2B/2C RECEPTOR ANTAGONISTS

This invention relates to compounds having pharmacological activity, processes for their preparation, to compositions containing them and to their use in the treatment of CNS disorders.

WO 92/05170, WO 94/04533, WO 94/14801, WO 95/01976 and J. Med. Chem., 1995, 38, 2524–2530 (SmithKline Beecham plc) describe indole and indoline derivatives which are described as possessing $5HT_{2C}$ receptor antagonist activity. Indole-3-carboxylic acid compounds having $5HT_3$ antagonist activity are diclosed in JPA 03 161 470. Indole derivatives having activity as tyrosine kinase inhibitors are disclosed in J. Med. Chem., 1995, 38, 58–57. Quinoline and indoline derivatives having potassium channel activating activity are disclosed in EPA 0 610 553 (E. R. Squibb).

A structurally distinct class of compounds has now been discovered, which have been found to have $5HT_{2C}$ receptor antagonist activity. Certain compounds of the invention also exhibit $5HT_{2B}$ antagonist activity. $5HT_{2C/2B}$ receptor antagonists are believed to be of potential use in the treatment of CNS disorders such as anxiety, depression, epilepsy, obsessive compulsive disorders, migraine, Alzheimers disease, sleep disorders, feeding disorders such as anorexia and bulimia, panic attacks, withdrawal from drug abuse such as cocaine, ethanol, nicotine and benzodiazepines, schizophrenia, and also disorders associated with spinal trauma and/or head injury such as hydrocephalus. Compounds of the invention are also expected to be of use in the treatment of certain GI disorders such as IBS.

The present invention therefore provides, in a first aspect, a compound of formula (I) or a salt thereof:

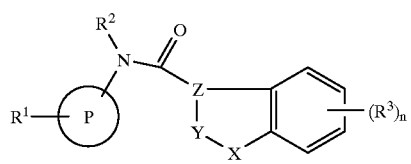

(I)

wherein:
P represents phenyl, a quinoline or isoquinoline residue, or a 5-membered or 6-membered aromatic heterocyclic ring containing up to three heteroatoms selected from nitrogen, oxygen or sulphur;

X and Y are independently selected from oxygen, sulphur, carbon, nitrogen, C=O, CH, $CH_2$ or $NR^4$ where $R^4$ is hydrogen or $C_{1-6}$ alkyl;

Z is carbon, nitrogen or CH and the dotted lines represent optional double bonds;

$R^1$ is hydrogen, $C_{1-6}$ alkyl, halogen, $CF_3$, $NR^7R^8$ or $OR^9$ where $R^7$, $R^8$ and $R^9$ are independently hydrogen or $C_{1-6}$ alkyl;

$R^2$ is hydrogen or $C_{1-6}$ alkyl;

n is 0 to 3; and $R^3$ groups are independently $C_{1-6}$ alkyl optionally substituted by one or more halogen atoms, $C_{2-6}$ alkenyl, $C_{2-6}$ alkynyl, $C_{3-6}$ cycloalkyl, $C_{3-6}$ cycloalkyl-$C_{1-6}$ alkyl, $C_{1-6}$ alkylthio, $C_{3-6}$cycloalkylthio, $C_{3-6}$ cycloalkyl$C_{1-6}$ alkylthio, halogen, nitro, $CF_3$, $OCF_3$, $SCF_3$, $SO_2CF_3$, $SO_2F$, formyl, $C_{2-6}$ alkanoyl, cyano, phenyl or thienyl optionally substituted by $C_{1-6}$ alkyl, halogen, $CF_3$, $NR^7R^8$ or $OR^9$ where $R^7$, $R^8$ and $R^9$ are independently hydrogen or $C_{1-6}$ alkyl, or $R^3$ is $NR^7R^8$, $CONR^7R^8$, or $OR^9$ where $R^7$, $R^8$ and $R^9$ are as defined for $R^1$, $CO_2R^{10}$ where $R^{10}$ is hydrogen or $C_{1-6}$ alkyl, provided that:
when X and Y are both $CH_2$, Z is other than nitrogen, when X, Y and Z form part of an indole ring, n is not zero.

$C_{1-6}$ Alkyl groups, whether alone or as part of another group, may be straight chain or branched.

The amide moiety can be attached to a carbon or any available nitrogen atom of the ring P, preferably it is attached to a carbon atom. Suitable moieties when the ring P is a 5-membered aromatic heterocyclic ring include isothiazolyl, isoxazolyl, thiadiazolyl and triazolyl. Suitable moieties when the ring P is a 6-membered aromatic heterocyclic ring include, for example, pyridyl, pyrimidyl or pyrazinyl. When P is quinoline, or an isoquinoline residue, the amide moiety can be attached at any position of the ring, preferably to the 4- or 5-position. Preferably P is 3-pyridyl, in particular 3-pyridyl.

Suitably X and Y are independently selected from oxygen, sulphur, carbon, nitrogen, C=O, CH, $CH_2$ or $NR^4$ where $R^4$ is hydrogen or $C_{1-6}$ alkyl and Z is selected from carbon, CH or nitrogen such that X, Y and Z together with the phenyl group to which they are attached form a 5,6 bicyclic ring system. Examples of such ring systems include benzothiophene, benzofuran, indene and indole. Preferably X is oxygen, sulphur or $NR^4$, Z is carbon and Y is CH, i.e. Z-Y is a C=CH group such that X, Y and Z together with the phenyl group to which they are attached form part of a benzofuran, benzothiophene or indole ring.

Preferably $R^1$ is hydrogen.
Preferably $R^2$ is hydrogen.
Suitably $R^3$ groups are independently $C_{1-6}$ alkyl optionally substituted by one or more halogen atoms, $C_{2-6}$ alkenyl, $C_{2-6}$ alkynyl, $C_{3-6}$ cycloalkyl, $C_{3-6}$ cycloalkyl-$C_{1-6}$ alkyl, $C_{1-6}$ alkylthio, $C_{3-6}$cycloalkylthio, $C_{3-6}$ cycloalkyl$C_{1-6}$ alkylthio, halogen, nitro, $CF_3$, $OCF_3$, $SCF_3$, $SO_2CF_3$, $SO_2F$, formyl, $C_{2-6}$ alkanoyl, cyano, phenyl or thienyl optionally substituted by $C_{1-6}$ alkyl, halogen, $CF_3$, $NR^7R^8$ or $OR^9$ where $R^7$, $R^8$ and $R^9$ are independently hydrogen or $C_{1-6}$ alkyl, or $R^3$ is $NR^7R^8$, $CONR^7R^8$, or $OR^9$ where $R^7$, $R^8$ and $R^9$ are as defined for $R^1$, $CO_2R^{10}$ where $R^{10}$ is hydrogen or $C_{1-6}$ alkyl. When two adjacent $R^3$ groups together form a 5-membered heterocyclic ring examples of such rings include thienyl, furyl and pyrrollyl rings. When n is greater than 1 the resulting $R^3$ groups can be the same or different. Preferably n is 2. Preferably an indoline, benzofuran or benzothiophene ring is disubstituted in the 5- and 6-positions. Preferably the 5-position is substituted by halogen or trifluoromethyl and the 6-position is substituted by $C_{1-6}$alkyl such as methyl or $C_{1-6}$alkoxy such as methoxy, or $C_{1-6}$alkylthio such as methylthio.

Particular compounds of the invention include:
5-Bromo-6-methoxy-N-(3-pyridyl)benzo-[b]thiophene-3-carboxamide,
6-Methoxy-N-(3-pyridyl)-5-trifluoromethylbenzo[b] thiophene-3-carboxamide,
5-Bromo-6-methoxy-N-(3-pyridyl)benzo-[b]furan-3-carboxamide,
6-Methoxy-N-(3-pyridyl)-5-trifluoromethylbenzo[b]furan-3-carboxamide,
5-Bromo-6-methoxy-N-(3-pyridyl)indole-3-carboxamide,
6-Methoxy-1-methyl-N-(3-pyridyl)-5-trifluoromethylindole-3-carboxamide,
5-chloro-6-methyl-N-(3-pyridyl)benzothiophene-3-carboxamide, 5-Thiomethyl-6-trifluoromethyl-1-(3-pyridylcarbamoyl)-indole, and pharmaceutically acceptable salts thereof.

The compounds of the formula (I) can form acid addition salts with acids, such as conventional pharmaceutically acceptable acids, for example maleic, hydrochloric, hydrobromic, phosphoric, acetic, fumaric, salicylic, citric, lactic, mandelic, tartaric and methanesulphonic acids.

Certain compounds of formula (I) may also form N-oxides or solvates such as hydrates, and the invention also extends to these forms. When referred to herein, it is understood that the term 'compound of formula (I)' also includes these forms.

Certain compounds of formula (I) are capable of existing in stereoisomeric forms including enantiomers and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

The present invention also provides a process for the preparation of a compound of formula (I) or a pharmaceutically acceptable salt thereof, which process comprises:
the coupling of a compound of formula (II);

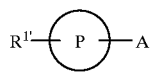

(II)

with a compound of formula (III):

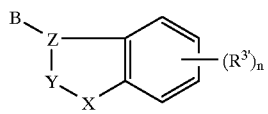

(III)

wherein n, X, Y, Z and P are as defined in formula (I), A and B contain the appropriate functional group(s) necessary to form the moiety —NR$^{2'}$CO when coupled, the variables R$^{1'}$, R$^{2'}$ and R$^{3'}$ are R$^1$, R$^2$, and R$^3$ respectively, as defined in formula (I), or groups convertible thereto, and thereafter optionally and as necessary and in any appropriate order, converting any R$^{1'}$, R$^{2'}$ and R$^{3'}$, when other than R$^1$, R$^2$ and R$^3$ respectively to R$^1$, R$^2$ and R$^3$, interconverting R$^1$, R$^2$ and R$^3$ and forming a pharmaceutically acceptable salt thereof.

Preferably A is —NHR$^{2'}$ and B is COL wherein R$^{2'}$ is as defined above and L is a leaving group. Such compounds can be reacted using standard chemistry. Examples of suitable compounds of formula (III) include acyl halides in which the leaving group L is halogen such as chloro. Activated compounds of formula (III) can also be prepared by reaction of the corresponding carboxylic acid with a coupling reagent such as carbonyldiimidazole, dicyclohexylcarbodiimide or diphenylphosphoryl azide.

R$^3$ groups can be introduced at any suitable stage in the process, preferably R$^3$ groups are introduced at an early stage in the process. It should be appreciated that it is preferred that all groups R$^1$ to R$^3$ are introduced before coupling compounds of formula (II) and (III).

Suitable examples of groups R$^{1'}$, R$^{2'}$ and R$^{3'}$ which are convertible to R$^1$, R$^2$ and R$^3$ alkyl groups respectively, include acyl groups which are introduced conventionally and may be converted to the corresponding alkyl group by conventional reduction, such as using sodium borohydride in an inert solvent followed by hydrogenolysis in an inert solvent. Hydrogen substituents may be obtained from alkoxycarbonyl groups which may be converted to hydrogen by hydrolysis and decarboxylation. When R$^3$ is hydroxy it is preferably protected in the compound of formula (II) as, for example, benzyl which is removed by hydrogenation.

Suitable examples of a group R$^{2'}$ which are convertible to R$^2$, include alkoxycarbonyl and benzyl or paramethoxybenzyl which are converted to the group where R$^2$ is hydrogen using conventional conditions.

Interconversions of R$^1$, R$^2$ and R$^3$ are carried out by conventional procedures. For example R$^1$ halo and R$^3$ halo may be introduced by selective halogenation of the ring P or the benzene ring of the indoline group using conventional conditions. It should be appreciated that it may be necessary to protect any R$^1$ to R$^3$ hydrogen variables which are not required to be interconverted.

Suitable protecting groups and methods for their attachment and removal are conventional in the art of organic chemistry, such as those described in Greene T. W. 'Protective groups in organic synthesis' New York, Wiley (1981).

Compounds of formula (II) in which A is NHR$^{2'}$ are known compounds or can be prepared analogously to known compounds. As mentioned above, compounds of formula (III) are prepared from the corresponding acids, that is to say, compounds of formula (IV):

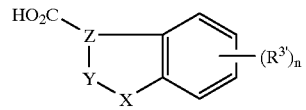

(IV)

in which n, X, Y, Z and R$^{3'}$ are as defined in formula (III). Compounds of formula (IV) are either commercially available or may be prepared according to known methods or analogous to known methods. Novel intermediates of formula (III) also form part of the invention.

Pharmaceutically acceptable salts may be prepared conventionally by reaction with the appropriate acid or acid derivative. N-oxides may be formed conventionally by reaction with hydrogen peroxide or percarboxylic acids.

Compounds of formula (I) and their pharmaceutically acceptable salts have 5HT$_{2B/2C}$ receptor antagonist activity and are believed to be of potential use fo the treatment or prophylaxis of CNS disorders such as anxiety, depression, epilepsy, obsessive compulsive disorders, migraine, Alzheimers disease, sleep disorders, feeding disorders such as anorexia and bulimia, panic attacks, withdrawal from drug abuse such as cocaine, ethanol, nicotine and benzodiazepines, schizophrenia, and also disorders associated with spinal trauma and/or head injury such as hydrocephalus. Compounds of the invention are also expected to be of use in the treatment of certain GI disorders such as IBS.

Thus the invention also provides a compound of formula (I) or a pharmaceutically acceptable salt thereof, for use as a therapeutic substance, in particular in the treatment or prophylaxis of the above disorders.

The invention further provides a method of treatment or prophylaxis of the above disorders, in mammals including humans, which comprises administering to the sufferer a therapeutically effective amount of a compound of formula (I) or a pharmaceutically acceptable salt thereof.

In another aspect, the invention provides the use of a compound of formula (I) or a pharmaceutically acceptable salt thereof in the manufacture of a medicament for the treatment or prophylaxis of the above disorders.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 0.05 to 20.0 mg, for example 0.2 to 5 mg; and such unit doses may be administered more than once a day, for example two or three a day, so that the total daily dosage is in the range of about 0.5 to 100 mg; and such therapy may extend for a number of weeks or months.

When administered in accordance with the invention, no unacceptable toxicological effects are expected with the compounds of the invention.

The following Descriptions and Examples illustrate the preparation of compounds of the invention.

DESCRIPTION 1

3-Methoxy-4-bromoaniline (D1)

2-Bromo-5-nitroanisole (31 g, 134 mmoles) in methanol (700 ml) was added to a mixture of iron powder (22.5 g, 400 mmoles), and ammonium chloride (33.5 g, 630 mmoles) in water (600 ml). The mixture was heated under reflux for 3 hrs. The mixture was allowed to cool and filtered. The filtrate was concentrated in vacuo and the residue partitioned between water and dichloromethane. The organic phase was dried ($Na_2SO_4$), filtered and evaporated to dryness to give the title compound (D1) (25 g, 93%).

NMR ($CDCl_3$) δ: 3.60–3.75 (2H, br s), 3.81 (3H, s), 6.12–6.19 (1H, m), 6.21 (1H, s), 7.23 (1H, d, J=8 Hz)

DESCRIPTION 2

3-Methoxy-4-bromobenzenethiol (D2)

3-Methoxy-4-bromoaniline (D1) (14.0 g, 69 mmoles) was diazotised in concentrated hydrochloric acid/ice-water 50:50 (40 ml) by treating with sodium nitrite (5.0 g, 72 mmoles). The diazonium salt was then added very slowly to a solution of ethyl potassium xanthate (12.2 g, 76 mmoles) in water (20 ml) at 55° C. The resulting xanthate ester was subjected to base hydrolysis followed by acid-base extraction to give the title compound (D2) (8.1 g, 53%)*

NMR ($CDCl_3$) δ: 3.50 (1H, s), 3.85 (3H, s), 6.71–6.82 (2H, m), 7.38 (1H, d, J=8 Hz.

* Detailed procedure: D. S. Tarbell, D. K. Fukushima, Organic Synthesis, Collective Volume III, p809.

DESCRIPTION 3

Ethyl 3-(3-methoxy-4-bromophenylthio)-2-oxopropanoate (D3)

3-Methoxy-4-bromobenzenethiol (D2) (9.6 g, 44 mmoles) in pyridine (30 ml) was treated with ethyl bromopyruvate (5.9 ml, 46 mmoles) and stirred at room temperature for 1 hr. Dilute hydrochloric acid (100 ml) was added and the product extracted into diethyl ether. The organics were washed with dilute hydrochloric acid then brine and dried ($Na_2SO_4$). Evaporation of the solvent followed by flash chromatography on TLC silica gel eluting with dichloromethane gave the title compound (D3) (3.7 g, 25%).

NMR ($CDCl_3$) δ: 1.25–1.45 (3H, m), 3.90 (3H, s), 4.25–4.40 (2H, m), 6.81–6.95 (2H, m), 7.41 (1H, d, J=8 Hz)

DESCRIPTION 4

Ethyl 5-bromo-6-methoxybenzo[b]thiophene-3-carboxylate (D4)

Ethyl 3-(3-methoxy-4-bromophenylthio)-2-oxopropanoate (D3) (3.7 g, 11 mmoles) in chlorobenzene (25 ml) was treated with phosphorus pentoxide (11.1 g, 78 mmoles) and 85% phosphoric acid (5.5 ml). The mixture was heated under reflux for 6 hrs. The mixture was allowed to cool and then partitioned between water (150 ml) and dichloromethane. The organics were washed several times with water then dried ($Na_2SO_4$). Evaporation to dryness followed by flash chromatography on TLC silica gel eluting with dichloromethane/60–80 petrol-ether 1:1 gave the title compound (D4) (0.94 g, 27%).

NMR ($CDCl_3$) δ: 1.42 (3H, t, J=8 Hz), 3.95 (3H, s), 4.40 (2H, q, J=8 Hz), 7.30 (1H, s), 8.20 (1H, s), 8.78 (1H, s).

DESCRIPTION 5

5-Bromo-6-methoxybenzo[b]thiophene-3-carboxylic acid (D5)

Ethyl 5-bromo-6-methoxybenzo[b]thiophene-3-carboxylate (D4) (0.42 g, 0.0013 mole) in ethanol (20 ml) and water (5 ml) was treated with sodium hydroxide powder (0.14 g, 0.0035 mole). The reaction mixture was heated under reflux for 2 hours and stirred at ambient temperature for 16 hours. The solvent was removed in vacuo and the residue diluted with water (25 ml), acidified with 5N hydrochloric acid, extracted into ethyl acetate, dried ($Na_2SO_4$) and evaporated in vacuo to afford the title compound (0.36 g, 93%) as a beige solid.

$^1$H NMR (200 MHz; $D^6$DMSO); δ: 3.08–3.60 (1H, br s), 3.93 (3H, s), 7.88 (1H, s), 8.52 (1H, s), 8.64 (1H, s).

DESCRIPTION 6

Ethyl 5-trifluoromethyl-6-methoxybenzo[b]thiophene-3-carboxylate (D6)

Ethyl-5-bromo-6-methoxybenzo[b]thiophene-3-carboxylate (D4) (0.81 g, 3 mmoles) in dry dimethylformamide (20 ml) and toluene (10 ml) was treated with potassium trifluoroacetate (0.78 g, 6 mmoles) and copper (I) iodide (0.98 g, 6 mmoles). The mixture was heated under reflux for 1 hr using a Dean-Stark trap to collect the toluene. The mixture was cooled and poured into water (150 ml) and extracted with diethyl ether. The resulting emulsion was filtered through kieselguhr. The combined organic extracts were washed several times with water then dried ($Na_2SO_4$). Flash chromatography on TLC silica gel eluting with dichloromethane/60–80 petrol ether 1:1 gave the title compound (D6) (0.5 g, 64%)

NMR ($CDCl_3$) δ: 1.45 (3H, t, J=8 Hz), 3.95 (3H, s), 4.40 (2H, q, J=8 Hz), 7.40 (1H, s), 8.25 (1H, s), 8.8 (1H, s)

DESCRIPTION 7

5-Trifluoromethyl-6-methoxybenzo[b]thiophene-3-carboxylic acid (D7)

Ethyl 5-trifluoromethyl-6-methoxybenzo[b]thiophene-3-carboxylate (D6) (0.5 g, 2 mmoles) was treated with sodium hydroxide as in the method of description 5 to give the title compound (D7) (0.42 g, 92%)

NMR (DMSO) δ: 3.95 (3H, s), 8.0 (1H, s), 8.58 (1H, s), 8.21 (1H, s), 13.11–13.21 (1H, br s)

DESCRIPTION 8

3-Methoxy-4-bromophenol (D8)

3-Methoxy-4-bromoaniline (D1) (10.0 g, 49 mmoles) in water (60 ml) and concentrated sulphuric acid (30 ml) was treated with a solution of sodium nitrite (3.4 g, 49 mmoles) in water (15 ml) dropwise keeping the temperature below 5° C. The resulting slurry was then added slowly to a mixture of water (60 ml) and concentrated sulphuric acid (30 ml) at 80° C. and stirred at this temperature for 3 hrs. The mixture was cooled and extracted with dichloromethane (2×200 ml). The organics were then extracted with 2N sodium hydroxide solutions (2×100 ml). The aqueous was washed with more dichloromethane (2×200 ml) then acidified to pH 1. Extraction with dichloromethane, drying ($Na_2SO_4$) and evaporation to dryness gave the title compound (D8) (6.95 g, 69%).

NMR ($CDCl_3$) δ: 3.85 (3H, s), 4.75–4.95 (1H, br s), 6.29–6.35 (1H, m), 6.45 (1H, s), 7.35 (1H, d, J=8 Hz).

DESCRIPTION 9

Ethyl 3-methoxy-4-bromophenoxyacetate (D9)

3-Methoxy-4-bromophenol D8 (6.95 g, 34 mmoles) in dry dimethylformamide (100 ml) at 0° C. was treated with sodium hydride (80% dispersion in oil) (1.13 g, 37 mmoles). After 30 mins ethyl bromoacetate (3.8 ml, 34 mmoles) was added and the mixture allowed to warm to room temperature over 1 hr. The mixture was concentrated in vacuo and the residue partitioned between water and diethyl ether. The organic layer was washed several times with water and then dried ($Na_2SO_4$) and evaporated to dryness. Flash chromatography on TLC silica gel eluting with dichloromethane gave the title compound (D9) (7.43 g, 75%)

NMR ($CDCl_3$) δ: 1.30 (3H, t, J=8 Hz), 3.85 (3H, s), 4.28 (2H, q, J=8 Hz), 6.28–6.32 (1H, m), 6.58 (1H, s), 7.40 (1H, d, J=10 Hz)

DESCRIPTION 10

Diethyl-3-methoxy-4-bromophenoxyoxalate (D10)

Diethyl oxalate (2.8 ml, 20 mmoles) was added to a suspension of sodium ethoxide (1.48 g, 21 mmoles) in dry diethyl ether (30 ml) and stirred at room temperature for 15 mins. A solution of ethyl-3-methoxy-4-bromophenoxyacetate (D9) (6.0 g, 20 mmoles) in diethyl ether (30 ml) was then added dropwise. The mixture was stirred at room temperature for 18 hrs then washed with 1N hydrochloric acid (2×100 ml), water (100 ml), brine (100 ml) then dried ($Na_2SO_4$). Evaporation of solvent gave the title compound (D10) (7.84 g, 97%).

NMR ($CDCl_3$) δ: 1.20–1.45 (6H, m), 3.80 (3H, s), 4.20–4.45 (4H, m), 6.31–6.42 (1H, m), 6.55–6.68 (1H, m), 7.37–7.45 (1H, m)

DESCRIPTION 11

Diethyl 5-bromo-6-methoxybenzo[b]furan-2,3-dicarboxylate (D11)

Diethyl 3-methoxy-4-bromophenoxyoxalacetate (D10) (7.8 g, 20 mmoles) was stirred with concentrated sulphuric acid (50 ml) for 30 mins. The mixture was then poured into ice water (500 ml) and extracted with diethyl ether (250 ml). The organics were washed with saturated aqueous sodium bicarbonate, dried ($Na_2SO_4$) and evaporated to dryness. Flash chromatography on TLC silica gel eluting with dichloromethane gave the title compound (D11) (3.29 g, 44%)

NMR ($CDCl_3$) δ: 1.37–1.50 (6H, m), 3.90 (3H, s), 4.39–4.53 (4H, m), 7.05 (1H, s), 8.07 (1H, s)

DESCRIPTION 12

5-Bromo-6-methoxybenzo[b]furan-2,3-dicarboxylic acid (D12)

Diethyl 5-bromo-6-methoxybenzo[b]furan-2,3-dicarboxylate (D11) (1.26 g, 3.4 mmoles) in ethanol (20 ml) and water (5 ml) was treated with 20% sodium hydroxide solution (5 ml) and heated under reflux for 3 hrs. The mixture was cooled and the ethanol removed in vacuo. The mixture was acidified to pH1 with hydrochloric acid. Filtration of the solid and drying gave the title compound (D12) (0.91 g, 85%)

NMR (DMSO-$d_6$) δ: 3.90 (3H, s), 7.50 (1H, s), 7.90–8.80 (3H including 2H, br s and 8.25 (1H, s))

DESCRIPTION 13

5-Bromo-6-methoxybenzo[b]furan-3-carboxylic acid (D13)

5-Bromo-6-methoxybenzo[b]furan-2,3-dicarboxylic acid (D12) (0.85 g, 2.7 mmoles) was heated to its melting point (~270° C.) for 15 mins ($CO_2$ evolution). The mixture was allowed to cool and the resulting black residue extracted with ethyl acetate. The organic solution was then filtered and the filtrate evaporated to dryness to give the title compound (D13) (0.65 g, 89%)

NMR (DMSO-$d_6$) δ: 3.90 (3H, s), 7.51 (1H, s), 8.02 (1H, s), 8.60 (1H, s).

DESCRIPTION 14

Ethyl 5-bromo-6-methoxybenzo[b]furan-3-carboxylate (D14)

5-Bromo-6-methoxybenzo[b]furan-3-carboxylic acid (D13) (0.27 g, 1 mmole) was heated under reflux for 1 hr in thionyl chloride. Cooling and evaporating to dryness gave the acid chloride which was treated with ethanol (10 ml) and triethylamine (1 ml). After 1 hr the mixture was evaporated to dryness and the residue partitioned between water and dichloromethane. The organic layer was dried ($Na_2SO_4$) and evaporated to dryness. Flash chromatography on TLC silica gel eluting with dichloromethane/60–80 petrol ether 50:50 gave the title compound (D14) (0.077 g, 26%)

NMR ($CDCl_3$) δ: 1.40 (3H, t, J=8 Hz), 3.90 (3H, s), 4.39 (2H, q, J=8 Hz), 7.03 (1H, s), 8.13 (1H, s), 8.19 (1H, s)

DESCRIPTION 15

Ethyl 5-trifluoromethyl-6-methoxybenzo[b]furan-3-carboxylate (D15)

Ethyl-5-bromo-6-methoxybenzo[b]furan-3-carboxylate (D14) (0.077 g, 0.3 mmoles) was converted to the title compound (D15) as in the method of description 6 (0.028 g, 38%)

NMR ($CDCl_3$) δ: 1.40 (3H, t, J=8 Hz), 3.92 (3H, s), 4.40 (2H, q, J=8 Hz), 7.10 (1H, s), 8.20 (1H, s), 8.28 (1H, s).

DESCRIPTION 16

5-Trifluoromethyl-6-methoxybenzo[b]furan-3-carboxylic acid (D16)

Ethyl 5-trifluoromethyl-6-methoxybenzo[b]furan-3-carboxylate (D15) (0.028, 0.1 mmoles) was hydrolysed to the title compound (D16) as in the method of description 5 (0.022 g, 90%)

DESCRIPTION 17

4-Bromo-3-methoxy-N-methylsulphonylanilide (D17)

Methanesulphonyl chloride (22.4 ml, 289 mmol) was added dropwise to a solution of aniline (D1, 56.1 g, 277.7 mmol) and pyridine (23.1 ml, 277.7 mmol) in dry dichloromethane (600 ml) at 0° C. The mixture was stirred overnight, then washed with water three times, dried and concentrated to crystallise the product. A further crop was obtained by addition of petrol to the mother liquor and further concentration. The two crops were combined to give the title compound (68.0 g, 87%) mp 121–4° C.

NMR ($CDCl_3$) δ: 3.03 (3H, s), 3.91 (3H, s), 6.79 (1H, dd, J=7,2), 6.89 (1H, d, J=2), 7.49 (1H, d, J=7)

DESCRIPTION 18

4-Bromo-N-(2,2-diethoxyethyl)-3-methoxy-N-methylsulphonyl anilide (D18)

A solution of sulphonylanilide (D17, 68.0 g, 243 mmol) in dimethyl-formamide (350 ml) was added over 40 min to a suspension of sodium hydride (80% in oil, 8.1 g, 269.5 mmol) in dimethylformamide (50 ml) at 0° C. After 30 min, when evolution of hydrogen had ceased, (2,2-diethoxyethyl) trifluoromethanesulphonate (77.8 g, 292.5 mmol) was added as a steady stream. After 6h at room temperature further quantities of sodium hydride (0.8 g) and trifluoromethane-sulphonate (8 g) were added, and stirring was continued overnight. The mixture was then partially evaporated, diluted with water and extracted with toluene. The organic extract was washed well with water and brine, dried and evaporated. The residue was recrystallised twice from dichloromethane/petrol to give the title compound (39 g, 40.5%), mp. 70–72° C.

NMR ($CDCl_3$) δ: 1.18 (3H, t, J=7), 2.97 (3H, s), 3.51 (2H, m), 3.67 (2H, m), 3.75 (2H, d, J=6), 3.90 (3H, s), 4.41 (1H, t, J=6), 6.83 (1H, dd, J=7, 2), 6.97 (1H, d, J=2), 7.54 (1H, d, J=7)

DESCRIPTION 19

5-Bromo-6-methoxy-1-methylsulphonylindole (D19)

A solution of titanium tetrachloride in toluene (138 ml of 1M solution diluted with 750 ml toluene) was added slowly to a solution of diethoxyethyl anilide (D18, 39 g, 98.4 mmol) in toluene (2.0 L) at 0° C. Internal temperature remained below 5° C. during addition. The mixture was then heated until reflux began, maintained at reflux for 10 min, then cooled, washed with sat. sodium bicarbonate solution, dilute hydrochloric acid and water, dried and evaporated. The residue was recrystallised from ether. The mother liquor was chromatographed on silica gel eluted with dichloromethane and eluted material was recrystallised from ether to give a second crop. The two crops were combined to give the title compound (21.2 g, 71%), mp. 126–129° C.

NMR ($CDCl_3$) δ: 3.09 (3H, s), 3.98 (3H, s), 6.61 (1H, d, J=3), 7.34 (1H, d, J=3), 7.48 (1H, s), 7.79 (1H, s)

DESCRIPTION 20

5-Bromo-6-methoxy indole (D20)

The 1-methylsulphonylindole (D19, 21.2 g, 69.7 mmol) was heated under reflux in a mixture of 10% aqueous sodium hydroxide solution (170 ml) and ethanol (1.0 L) for 1.5 h. The mixture was evaporated almost to dryness, and the residue was dissolved in ethyl acetate and washed with water. The organic phase was dried and evaporated to give the title compound (15.65 g, 99%), mp 110–111° C.

NMR ($CDCl_3$) δ: 3.90 (3H, s), 6.43 (1H, m), 6.91 (1H, s), 7.10 (1H, m), 7.80 (1H, s), 8.18 (1H, broad)

DESCRIPTION 21

5-Bromo-6-methoxy-3-trichloroacetyl indole (D21)

Trichloroacetyl chloride (8.5 ml, 76.1 mmol) was added to a solution of pyridine (6.1 ml, 76.1 mmol) in dry 1,4-dioxan (70 ml). After a few minutes of stirring, a solution of indole (D20, 15.65 g, 69.2 mmol) in 1,4-dioxan (70 ml) was added slowly. The mixture was stirred for 24 h at room temperature, then poured into water. The precipitate was filtered off and washed with water, then recrystallised from ethanol/water to give the title compound (14.19 g, 55%), mp. 185–190° C.

NMR ($CDCl_3$/$CD_3OD$) δ: 3.93 (3H, s), 6.97 (1H, s), 8.24 (1H, s), 8.58 (1H, s)

DESCRIPTION 22

5-Bromo-6-methoxyindole-3-carboxylic acid (D22)

The trichloroacetylindole (D21, 1.48 g, 4 mmol) was heated in a mixture of 10% aqueous potassium hydroxide (3 ml) and tetrahydrofuran (15 ml) at 40–50° C. over three nights. The mixture was poured into water and extracted with ether. The ethereal phase was re-extracted with dil. potassium hydroxide solution, and the combined aqueous phases were acidified with 10% aq. hydrochloric acid and extracted with dichloromethane/methanol. This extract was dried and evaporated to give the title compound (0.74 g, 68.5%)

NMR ($CD_3OD$) δ: 3.90 (3H, s), 7.07 (1H, s), 7.87 (1H, s), 8.19 (1H, s)

DESCRIPTION 23

5-Bromo-6-methoxy-1methyl-3-trichloroacetylindole (D23)

The trichloroacetylindole (D21, 1.86 g, 5 mmol) was added in small portions to a suspension of sodium hydride (80% in oil, 0.165 g, 5.5 mmol) in dry dimethylformamide (20 ml). After stirring at room temperature for 20 min., methyl iodide (0.34 ml, 5.5 mmol) was added. After stirring for 1 h, the mixture was partially evaporated and the residue was poured into water. The precipitate was filtered off, washed with water and dried to give the title compound (1.75 g, 91%)

NMR ($CDCl_3$) δ: 3.88 (3H, s), 3.98 (3H, s), 6.80 (1H, s), 8.09 (1H, s), 8.60 (1H, s).

DESCRIPTION 24

Methyl 5-bromo-6-methoxy-1-methylindole-3-carboxylate (D24)

The trichloroacetylindole (D23, 1.73 g, 4.5 mmol) was heated under reflux in methanol (20 ml) containing 1 drop of 60% aqueous potassium hydroxide for 45 min. The mixture was then evaporated and the residue was slurried with water. The solid was filtered off and washed with water, then chromatographed on silica gel eluted with 0–2% methanol/dichloromethane to give the title compound (1.03 g, 77%)

NMR ($CDCl_3$) δ: 3.79 (3H, s), 3.91 (3H, s), 3.96 (3H, s), 6.76 (1H, s), 7.67 (1H, s), 8.30 (1H, s)

DESCRIPTION 25

Methyl 6-methoxy-1-methyl-5-trifluoromethylindole-3-carboxylate (D25)

A mixture of methyl ester (D24, 1.01 g, 3.4 mmol), potassium trifluoroacetate (1.04 g, 6.8 mmol) and copper (I) iodide (1.27 g, 6.8 mmol) in toluene (10 ml) and dimethylformamide (20 ml) was heated to distil off toluene. The mixture was then heated at 148–150° C. (internal) for 2 h. A further quantity of potassium trifluoroacetate (0.5 g) was added and heating continued for 2 h. The mixture was then evaporated and the residue was extracted with dichloromethane/methanol. The extract was filtered, washed with water, dried and evaporated. The residue was recrystallised from dichloromethane/petrol to give the title compound (0.67 g, 69%), mp. 166–170° C.

NMR ($CDCl_3$) δ: 3.81 (3H, s), 3.92 (3H, s), 3.97 (3H, s), 6.81 (1H, s), 7.73 (1H, s), 8.37 (1H, s).

DESCRIPTION 26

6-Methoxy-1-methyl-5-trifluoromethylindole-3-carboxylic acid (D26)

The trifluoromethylindole ester (D25, 0.67 g, 2.33 mmol) was heated under reflux in a mixture of 10% aqueous sodium hydroxide (5 ml) and methanol (10 ml) for 30 min. The mixture was then diluted with water to dissolve all solid and extracted with dichloromethane. The aqueous phase was acidified with 5M hydrochloric acid and the precipitate was filtered off and dried to give the title compound (0.56 g, 88%), mp. >247° C. (decomp.)

NMR ($d_6$-DMSO) δ: 3.86 (3H, s), 3.94 (3H, s), 7.34 (1H, s), 8.03 (1H, s), 8.22 (1H,s)

DESCRIPTION 27

5-Chloro-6-methylbenzo [b] thiophene (D27)

The title compound was prepared by adding (3-methyl-4-chlorophenylthio)acetaldehyde diethyl acetal to polyphosphoric acid under reduced pressure (1.5 mm Hg).* This gave 1.8 g of a mixture of the title compound (D27) and 4-methyl-5-chlorobenzo[b]thiophene in a 60:40 ratio.

* M. S. El Shanta and R. M. Scrawston, J. Chem. Soc. (C) 1967, 2084

NMR ($CDCl_3$) δ: 2.40 (3H, s), 7.12 (1H, d, J=6), 7.29 (1H, d, J=6), 7.61 (1H, s), 7.70 (1H, s)+peaks for undesired isomer.

DESCRIPTION 28

5-Chloro-6-methylbenzo [b] thiophene-3-carboxylic acid (D28)

Friedel-Crafts acylation of the mixture containing 5-chloro-6-methylbenzo [b] thiophene (D27) and 4-methyl-5-chlorobenzo [b] thiophene with trichloroacetyl chloride/aluminium chloride followed by basic hydrolysis* gave the title compound (D28) (0.09 g, 24%)

* R. Bonjouklian, Syn. Comm., 1985, 15(8), 711–713

NMR (DMSO-$d_6$) δ: 2.40 (3H, s), 7.89 (1H, s), 8.00 (1H, s), 8.82 (1H, s).

EXAMPLE 1

5-Bromo-6-methoxy-N-(3-pyridyl)benzo-[b]thiophene-3-carboxamide (E1)

5-Bromo-6-methoxybenzo[b]thiophene-3-carboxylic acid (D5) (0.36 g, 0.0013 mole) and thionyl chloride (20 ml) were heated under reflux for 1 hour, after which the reaction mixture was cooled to ambient temperature and evaporated in vacuo. The resulting acid chloride was dissolved in dry dichloromethane (30 ml) and acetonitrile (10 ml) under argon. 3-Aminopyridine (0.12 g, 0.0013 mole) was added and the reaction mixture stirred at ambient temperature for 16 hours. The solvent was removed in vacuo and the resulting solid basified with 10% sodium hydroxide solution, extracted into dichloromethane, dried ($Na_2SO_4$) and evaporated in vacuo. The resulting solid was recrystallised from ethyl acetate/methanol to afford the title compound (0.11 g, 23%) as a beige solid.

$^1$H NMR (270 MHz; $D^6$DMSO) δ: 3.93 (3H, s), 7.42 (1H, q), 7.89 (1H, s), 8.20 (1H, dt), 8.34 (1H, d), 8.56 (1H, s), 8.64 (1H, s), 8.93 (1H, s), 10.55 (1H, s)

EXAMPLE 2

6-Methoxy-N-(3-pyridyl)-5-trifluoromethylbenzo[b]thiophene-3-carboxamide hydrochloride salt (E2)

5-Trifluoromethyl-6-methoxybenzo[b]thiophene-3-carboxylic acid (D7) (0.39 g, 1.4 mmoles) was converted to the title compound as in the method of example 1 isolating as the hydrochloride salt after recrystallising from methanol. (E2) (0.33 g, 58%) m.p. >270° C.

NMR (DMSO-d$_6$) δ: 3.97 (3H, s), 7.91–7.99 (1H, m), 8.03 (1H, s), 8.62 (1H, d, J=6 Hz), 8.72 (1H, s), 8.81 (1H, d, J=6 Hz), 9.01 (1H, s), 9.41 (1H, s), 11.51 (1H, s), M$^+$=352; C$_{16}$H$_{11}$N$_2$O$_2$SF$_3$ requires 352

EXAMPLE 3

5-Bromo-6-methoxy-N-(3-pyridyl)benzo[b]furan-3-carboxamide (E3)

5-Bromo-6-methoxybenzo[b]furan-3-carboxylic acid (D13) (0.4 g, 1.4 moles) was converted to the title compound (E3) as in the method of example 1 (0.29 g, 58%) m.p. 210–212° C.

NMR (DMSO-d$_6$) δ: 3.91 (3H, s), 7.38–7.42 (1H, m), 7.52 (1H, s), 8.10–8.17 (1H, m), 8.20 (1H, s), 8.29–8.33 (1H, m), 8.70 (1H, s), 8.88 (1H, s). M$^+$=346 and 348, C$_{15}$H$_{11}$N$_2$O$_3$Br requires 346 and 348

EXAMPLE 4

6-Methoxy-N-(3-pyridyl)-5-trifluoromethylbenzo[b]furan-3-carboxamide (E4)

5-Trifluoromethyl-6-methoxybenzo[b]furan-3-carboxylic acid (D16) (0.025 g, 0.1 mmoles) was converted to the title compound as in the method of example 1 (0.025 g, 83%) mp. 219–221° C.

NMR (DMSO-d$_6$) δ: 3.95 (3H, s), 7.35–7.42 (1H, m), 7.65 (1H, s), 8.12 (1H, d, J=8 Hz), 8.25–8.39 (2H, m), 8.80 (1H, s), 8.90 (1H, s)

EXAMPLE 5

5-Bromo-6-methoxy-N-(3-pyridyl)indole-3-carboxamide (E5)

To a solution of acid (D22, 0.86 g, 3.2 mmol) in dry tetrahydrofuran (30 ml) was added oxalyl chloride (0.27 ml, 3.2 mmol) and dimethylformamide (3 drops). After stirring for 1 h at room temperature the mixture was evaporated. Fresh tetrahydrofuran (30 ml) was added, followed by a solution of 3-aminopyridine (0.30 g, 3.2 mmol) and triethylamine (0.44 ml, 3.2 mmol) in tetraydrofuran (10 ml). The mixture was stirred at room temperature overnight, then evaporated. The residue was dissolved in dichloromethanel-methanol and this solution was washed with water, saturated aqueous potassium carbonate and brine, dried and evaporated. The crude product was chromatographed on silica gel eluted with 10% methanol/dichloromethane to give the title compound (0.29 g, 26%), mp. >250° C.

NMR (d$_6$-DMSO) δ: 3.88 (3H, s), 7.15 (1H, s), 7.38 (1H, dd, J=7, 5), 8.19 (1H, dm, J=7), 8.27 (2H, m), 8.33 (1H, s), 8.90 (1H, d, J=2), 9.96 (1H, s), 11.77 (1H, s).

MS (EI) m/e=347 (M$^+$)

EXAMPLE 6

6-Methoxy-1-methyl-N-(3-pyridyl)-5-trifluoromethylindole-3-carboxamide (E6)

This compound was prepared by the method of Example 5, from acid (D26, 0.55 g, 2.0 mmol) and 3-aminopyridine (0.19 g, 2.0 mmol), with other reagents and solvents in proportionate quantities. After addition of the aminopyridine, the mixture was stirred for 4 h at room temperature, then poured into water. The precipitate was filtered off, washed with water and dried. The crude product was recrystallised from dichloromethane/methanol to give the title compound (0.55 g, 79%), mp. >250° C.

NMR (d$_6$-DMSO) δ: 3.92 (3H, s), 3.97 (3H, s), 7.39 (2H, m), 8.20 (1H, d, J=8), 8.28 (1H, d, J=5), 8.31 (1H, s), 8.45 (1H, s), 8.90 (1H, d, J=2), 10.07 (1H, s); MS (EI) m/e=349 (M$^+$)

EXAMPLE 7

5-Chloro-6-methyl-N-(3-pyridyl)benzo[b]thiophene-3-carboxamide hydrochloride (E7)

5-Chloro-6-methylbenzo[b]thiophene-3-carboxylic acid (D2) (0.09 g, 0.4 mmoles) was treated with thionyl chloride (10 ml) and heated under reflux for 2 hrs. The mixture was evaporated to dryness and the resulting acid chloride was re-dissolved in dichloromethane (10 ml) and treated with 3-acinopyridine (0.038 g, 0.4 mmoles). After 4hrs the precipitate was filtered off. Recrystallisation from methanol gave the title compound (E1) (0.04 g, 30%) m.p. 160–1° C.

NMR (DMSO-d$_6$) δ: 2.45 (3H, s), 7.73–7.81 (1H, m), 8.11 (1H, s), 8.47–8.53 (3H, m), 8.80 (1H, s), 9.20 (1H, s), 11.01 (1H, s). Found M$^+$302, 304; C$_{15}$H$_{11}$N$_2$O5Cl requires 302, 304

EXAMPLE 8

5-Thiomethyl-6-trifluoromethyl-1-(3-pyridylcarbamoyl)-indole (E8)

A solution of 5-methylthio-1-(3-pyridylcarbamoyl)-6-trifluoromethyl indoline (WO 95/01976) (500 mg, 1.4 mmol) in acetic acid (10 ml) under argon atmosphere was treated with manganese triacetate (415 mg, 1.53 mmol) and heated under reflux for 4 days. Work-up of the solution (neutralisation of the solution with sodium bicarbonate solution, filtration and extraction of the aqueous into dichloromethane) afforded a mixture which was separated by HPLC to yield a green powder (20 mg).

$^1$H NMR 250 MHz d$^6$-DMSO δ: 2.51 (s, 3H), 6.88 (d, 2H), 7.45 (m, 1H), 7.84 (s, 1H), 8.09 (m, 1H), 8.26 (d, 1H), 8.38 (d, 1H), 8.60 (s, 1H), 8.80 (m, 1H). Mass. spec. M$^+$ m/z=351 (10%)

PHARMACOLOGICAL DATA

[$^3$H]-mesulergine binding to rat or human 5-HT$_{2C}$ clones expressed in 293 cells in vitro Compounds were tested following the procedure outlined in WO 94/04533.

The compounds of examples 3 to 8 have pK$_i$ values of at least 7.2

We claim:

1. A compound of formula (I) or a salt thereof:

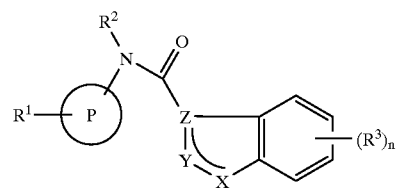

(I)

wherein:

P represents pyridyl;

X and Y are independently selected from oxygen, sulphur, nitrogen, CH, CH$_2$ or NR$^4$ where R$^4$ is hydrogen or C$_{1-6}$ alkyl;

Z is carbon, nitrogen or CH and the dotted lines represent optional double bonds;

$R^1$ is hydrogen, $C_{1-6}$ alkyl, halogen, $CF_3$, $NR^7R^8$ or $OR^9$ where $R^7$, $R^8$ and $R^9$ are independently hydrogen or $C_{1-6}$ alkyl;

$R^2$ is hydrogen or $C_{1-6}$ alkyl;

n is 0 to 3; and $R^3$ groups are independently $C_{1-6}$ alkyl optionally substituted by one or more halogen atoms; $C_{2-6}$ alkenyl, $C_{2-6}$ alkynyl, $C_{3-6}$ cycloalkyl, $C_{3-6}$ cycloalkyl-$C_{1-6}$ alkyl, $C_{1-6}$ alkylthio, $C_{3-6}$cycloalkylthio, $C_{3-6}$ cycloalkyl$C_{1-6}$ alkylthio, halogen, nitro, $CF_3$, $OCF_3$, $SCF_3$, $SO_2CF_3$, $SO_2F$, formyl, $C_{2-6}$ alkanoyl, cyano, phenyl or thienyl optionally substituted by $C_{1-6}$ alkyl, halogen, $CF_3$, $NR^7R^8$ or $OR^9$ where $R^7$, $R^8$ and $R^9$ are independently hydrogen or $C_{1-6}$ alkyl, or $R^3$ is $NR^7R^8$, $CONR^7R^8$, or $OR^9$ where $R^7$, $R^8$ and $R^9$ are as defined for $R^1$, $CO_2R^{10}$ where $R^{10}$ is hydrogen or $C_{1-6}$ alkyl, provided that:

when X and Y are both $CH_2$, Z is other than nitrogen, when X, Y and Z form part of an indole ring, n is not zero.

2. A compound according to claim 1 in which $R^1$ is hydrogen.

3. A compound according to claim 1 in which $R^2$ is hydrogen.

4. A compound according to claim 1 in which n is 2.

5. A compound according to claim 1 which is:

5-Bromo-6-methoxy-N-(3-pyridyl)benzo-[b]thiophene-3-carboxamide,

6-Methoxy-N-(3-pyridyl)-5-trfuoromethylbenzo[b]thiophene-3-carboxamide,

5-Bromo-6-methoxy-N-(3-pyridyl)benzo-[b]furan-3-carboxamide,

6-Methoxy-N-(3-pyridyl)-5-trifluoromethylbenzo[b]furan-3-carboxamide,

5-Bromo-6-methoxy-N-(3-pyridyl)indole-3-carboxamide,

6-Methoxy-1-methyl-N-(3-pyridyl)-5-trifluoromethylindole-3-carboxamide, 5-chloro-6-methyl-N-(3-pyridyl)benzothiophene-3-carboxamide, 5-Thiomethyl-6-trifluoromethyl-1-(3-pyridylcarbamoyl)-indole, and pharmaceutically acceptable salts thereof.

6. A pharmaceutical composition which comprises a compound according to claim 1 and a pharmaceutically acceptable carrier or excipient.

7. A method of treatment of CNS and IBS which comprises administering to a sufferer a therapeutically effective amount of a compound of formula (I) as defined in claim 1 or a pharmaceutically acceptable salt thereof.

8. A process for the preparation of a compound of formula (I) or a pharmaceutically acceptable salt thereof, which process comprises:

the coupling of a compound of formula (II);

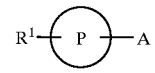

(II)

with a compound of formula (III);

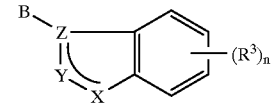

(III)

wherein n, X, Y, Z and P are as defined in formula (I), A is a group $NHR^2$ and B is COL where $R^1$, $R^2$, and $R^3$ are as defined in formula (I) and L is a leaving group; and thereafter forming a pharmaceutically acceptable salt thereof.

* * * * *